United States Patent [19]

Macovski

[11] Patent Number: 4,662,379
[45] Date of Patent: May 5, 1987

[54] CORONARY ARTERY IMAGING SYSTEM USING GATED TOMOSYNTHESIS

[75] Inventor: Albert Macovski, Menlo Park, Calif.

[73] Assignee: Stanford University, Stanford, Calif.

[21] Appl. No.: 902,086

[22] Filed: Aug. 27, 1986

Related U.S. Application Data

[63] Continuation of Ser. No. 684,069, Dec. 20, 1984, abandoned.

[51] Int. Cl.$^4$ .......................... A61B 6/02; G03B 41/16
[52] U.S. Cl. ......................................... 128/653; 378/5; 378/15
[58] Field of Search .................... 378/9, 11, 15, 21–22

[56] References Cited

U.S. PATENT DOCUMENTS

| | | | |
|---|---|---|---|
| 4,182,311 | 1/1980 | Seppi et al. | 128/653 |
| 4,204,124 | 5/1980 | Kowalski | 378/9 |
| 4,503,459 | 3/1985 | Nishimura | 128/653 X |
| 4,503,461 | 3/1985 | Haendle et al. | 128/653 X |
| 4,598,369 | 7/1986 | Wang et al. | 378/22 X |

OTHER PUBLICATIONS (author unknown) "Tomographic DSA Said to Reduce Motion Artifacts" *Diagnostic Imaging*, Jan. 1986 p. 11.
Haaken, P. et al., "A New Digital Tomosynthesis Method with Less Artifacts for Argiography", Med. Phys. 12(4), Jul/Aug. 1985 pp. 431–436.

*Primary Examiner*—Kyle L. Howell
*Assistant Examiner*—Francis Jaworski
*Attorney, Agent, or Firm*—Flehr, Hohbach, Test, Albritton & Herbert

[57] ABSTRACT

A method of imaging a blood vessel such as a coronary artery includes the steps of a dual energy providing radiation source and a radiation detector on opposing sides of a target area and at a plurality of angular positions through the target area. The radiation source is gated at the plurality of positions after administering a contrast agent intravenously to obtain a first plurality of detector signals indicative of a first plurality of views through said target area. The first plurality of detector signals are then tomosynthesisly combined to provide a planar image through the target area. Preferably, the gating of the radiation source after administering a contrast agent includes gating based on a selected time using an electrocardiogram, and the gating is at at least two energy levels to obtain detector signals at each energy level indicative of said plurality of views. Soft tissue is eliminated by combining signals at the least two image levels.

5 Claims, 2 Drawing Figures

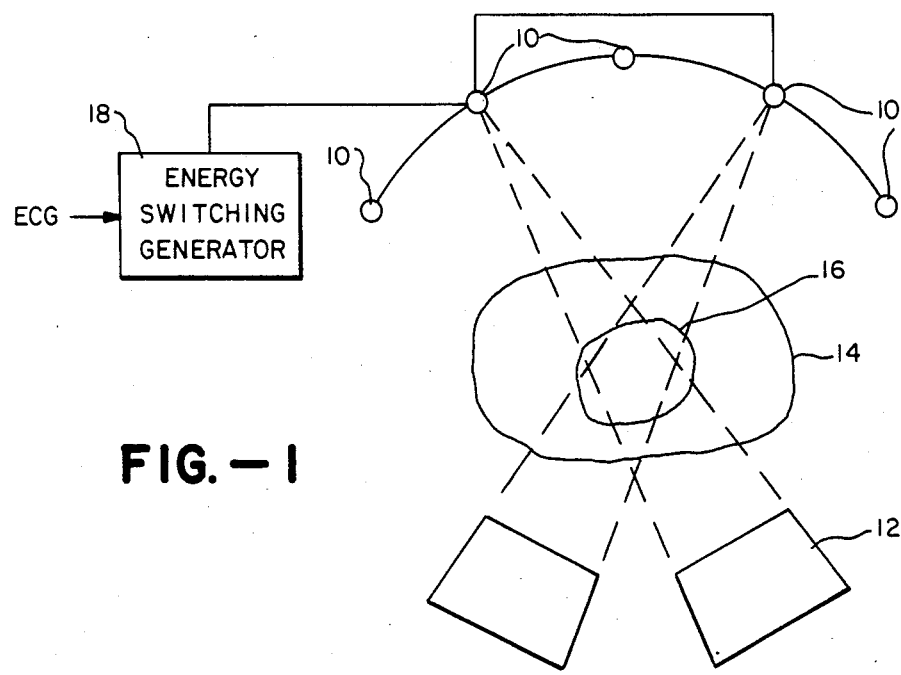
FIG. — 1
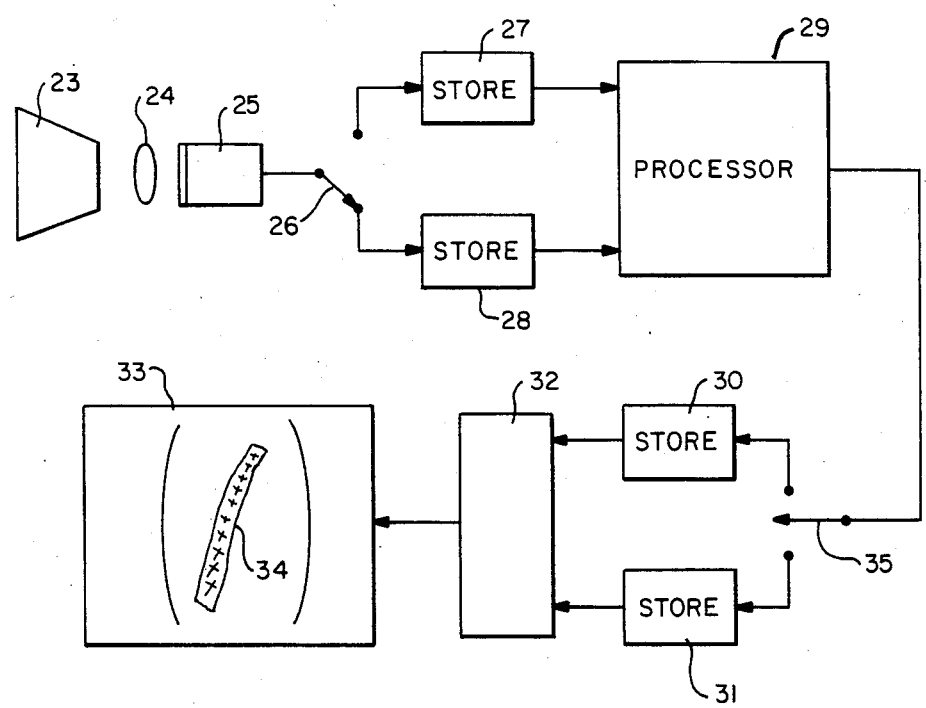
FIG. — 2

CORONARY ARTERY IMAGING SYSTEM USING GATED TOMOSYNTHESIS

The U.S. Government has rights in the invention disclosed and claimed herein pursuant to NIH Contract No. 1 HV 02922.

This is a continuation of application Ser. No. 684,069 filed Dec. 20, 1984, and now abandoned.

This invention relates generally to projection radiography, and more particularly the invention relates to a radiographic system and method useful in imaging the coronary arteries.

Various techniques using an iodinated contrast agent are known for non-invasive imaging of blood vessels. U.S. Pat. No. 3,843,130 issued to Macovski discloses a method of multiple energy X-ray imaging in which a selected material, such as soft tissue, can be eliminated. U.S. Pat. No. 4,029,966 issued to Alvarez and Macovski discloses non-linear processing of low and high energy projection measurements to produce atomic number dependent and density dependent projection information.

U.S. Pat. No. 4,445,226 issued to Brody discloses a method of eliminating soft tissue and bone structure from the image by a hybrid subtraction technique. U.S. Pat. No. 4,463,375 issued to Macovski combines a low pass filtered signal of a material selective image, as in Brody, with a high pass filtered signal having an improved signal to noise ratio to produce a weighted sum selective image with improved signal to noise ratio.

Imaging of the coronary arteries has been particularly difficult using known techniques because of the positioning of the arteries along the outer wall of the heart whereby iodinated blood in the heart obscures the iodinated blood in the arteries. Further, motion artifacts are introduced by the movement of the heart.

Accordingly, an object of the present invention is an improved method of imaging the coronary arteries.

In accordance with the present invention a gated tomosynthesis apparatus is provided for imaging the coronary arteries. Tomosynthesis is a known technique for imaging a plane in a target by blurring other planes in the target. In classical tomography, the X-ray source and detector move synchronously and continuously in opposite directions about a fulcrum residing in the plane of interest. This procedure produces an image or tomogram of the desired plane by blurring the contributions of the other planes. In the related tomosynthesis technique, a set of component radiographs is generated by pulsing the source at discrete intervals along the path used in classical tomography. After the exposure, these component images are superimposed and translated with respect to each other to synthesize a tomogram analogous in nature with those obtained in classical tomography. The plane of focus is selectable, varying continuously with the degree of translation. Hence, tomosynthesis is designed to enhance visualization of structure by blurring features in outlying regions. However, tomosynthesis enables arbitrarily many planes to be viewed from just a single exposure sequence, thus reducing the dose and examination time for typical studies. See Nishimura, Macovski, and Brody "Digital Tomosynthesis Using a Scanned Projection Radiographic System", SPIE, Vol. 314, Digital Radiography (1981), pp. 31–36.

In carrying out the invention a fluoroscopic system used to image the region of the coronary arteries is rotated to provide an array of multiple views. The X-rays are gated during the same portion of the heart cycle using electrocardiogram (ECG) gating. Approximately 5–10 positions can be achieved in one breath holding period. Additional positions can be achieved in a breath holding period by use of two X-ray sources.

The image data are combined in tomosynthesis fashion to provide an image of the plane containing the desired coronary arteries. The multiple images improve the signal-to-noise ratio while the plane selection blurs out the heart chambers and pulmonary vessels. The intervening soft tissue is removed by using dual energy at each source position in accordance with conventional techniques, supra. Soft tissue images are cancelled by combining the dual energy measurements, while intervening bone will be blurred by the tomosynthesis. Bone cancellation can be enhanced by using hybrid subtraction or triple energy measurements as noted above.

To reduce the total acquisition time when using hybrid subtraction, the first set of dual energy data, taken before administering the contrast agent, need not be timed to the ECG. This data is used solely for bone subtraction since soft tissue motion is removed by the dual energy processing.

The invention and objects and features thereof will be more readily apparent from the following detailed description and appended claims when taken with the drawing, in which:

FIG. 1 is a schematic illustration of a rotatable radiation source and detector in accordance with the invention.

FIG. 2 is a functional block diagram of signal storage, processing, and display apparatus in carrying out the invention.

Referring now to the drawing, FIG. 1 is a schematic illustration of an X-ray source 10 and fluoroscopic detector 12 which are rotatably mounted on opposing sides of a patient 14 for viewing a target area 16. The radiation source 10 provides a low energy spectrum of about 40–70 Kev and a high energy spectrum of about 70–120 Kev. The source 10 is gated by an energy switching generator 18 which is controlled by ECG gating during the same portion of the heart cycle. This gating can either control the X-ray generator or the grid of a grid controlled X-ray tube.

In carrying out the invention, a contrast agent is introduced intravenously and the source and detector are rotated to 5–10 positions within an angle of about 30° with image data being generated by the detector 12 at each position. It is desirable that all of the data be acquired within a breath holding interval to avoid bone motion. Two X-ray sources can be used to double the number of positions either with two imaging change or with a single image intensifier. In the latter case the X-ray tubes are switched in sequence.

As illustrated in the functional block diagram in FIG. 2, the detector includes an image intensifier 23. The resultant light image is projected through lens 24 onto a television camera 25. The projection measurements corresponding to each energy spectra are then directed through switch 26 and stored on storage systems 27 and 28. These are digital storage systems with capacity for storing the image data for each of the plurality of positions of the source.

The high energy data and low energy data are then applied to a processor 29 which combines the data in accordance with the teachings of U.S. Pat. No. 4,029,963 to eliminate soft tissue movement. The resultisng processed information can be combined using known tomosynthesis techniques to project an image of a selected plane through the target area. The multiple images improve the signal to noise ratio while the plane selection blurs out the heart chambers and pulmonary vessels. The intervening bone will be blurred by the tomosynthesis since the bone structure will lie outside of the plane of the coronary arteries.

To further remove image data resulting from bone structure, hybrid subtraction or triple energy measurements can be employed as disclosed in U.S. Pat. No. 4,445,226. In carrying out the hybrid subtraction, high and low energy measurements must be made at the several source positions both before administering the contrast agent and after administering the contrast agent. The data obtained before administering the contrast agent is processed by processor 29 and stored in memory 30, and the data obtained after administering the contrast agent is processed by processor 29 and stored in memory 31. The stored data is then combined by hybrid subtraction at 32 using the technique of U.S. Pat. No. 4,445,226, supra.

The total acquisition time of the first set of dual energy data, taken before applying the contrast agent, need not be timed to the ECG since it is used solely for bone subtraction. Any soft tissue motion is removed by the dual energy processing. Alternatively, a triple energy system can be used at each position enabling the simultaneous cancellation of both bone and soft tissue.

The described mechanically scanned fluoroscopy system with ECG gating enables non-invasive images to be obtained of small vessels including the coronary arteries. The tomosynthesis reconstruction of the plurality of images improves the signal to noise ratio and diminishes the contributions of background tissue such as the heart when imaging the coronary arteries. Motion is eliminated by the dual energy system, and bone structure can be eliminated by the hybrid subtraction or triple energy system if the tomosynthesis blurring is insufficient.

While the invention has been described with reference to a specific embodiment, the description is illustrative of the invention and is not to be construed as limiting the invention. Various modifications and applications may occur to those skilled in the art without departing from the true spirit and scope of the invention as defined by the appended claims.

What is claimed is:

1. A method of imaging a blood vessel such as a coronary artery comprising the steps of
    providing radiation source means and radiation detector means on opposing sides of a target area and at a plurality of administering a contrast agent intravenously,
    gating said radiation source means based on a selected time using an electrocardiogram to obtain a first plurality of detector signals indicative of a first plurality of views through said target area and,
    tomosynthesisly combining said first plurality of detector signals to provide a planar image through said target area, said planar image being generally perpendicular to the path of radiation through said target area.

2. The method as defined by claim 1 wherein said step of gating said radiation source includes gating said radiation source at at least two energy levels to obtain detector signals at each energy level indicative of said plurality of views, and further including the step of eliminating soft tissue by combining signals at said at least two image levels.

3. The method as defined by claim 2 and further including the step of gating said radiation source means at said plurality of positions prior to administering a contrast agent intravenously to obtain a second plurality of detector signals indicative of a second plurality of views through said target area, said step including gating said radiation source at said at least two energy levels to obtain detector signals at each energy level indicative of said plurality of views, said first plurality of detector signals and said plurality of detector signals being combined by hybrid subtraction.

4. The method as defined by claim 1 and further including the step of gating said radiation source means at said plurality of positions prior to administering said contrast agent intravenously to obtain a second plurality of detector signals indicative of a second plurality of views through said target area, said step including gating said radiation source at said at least two energy levels to obtain detector signals at each energy level indicative of said plurality of views, said first plurality of detector signals and said plurality of detector signals being combined by hybrid subtraction.

5. Apparatus for imaging a blood vessel such as a coronary artery comprising
    radiation source means and radiation detector means positioned on opposing sides of a target area and at a plurality of angular positions through the target area,
    means for gating said radiation source means at said plurality of positions including means responsive to an electrocardiogram for gating said source means at a selected time during a heart-beat for obtaining a first pluralitiy of detector signals indicative of a first plurality of views through said target area, and
    tomosynthesis means for combining said first plurality of detector signals to provide a planar image through said target area, said planar image being generally perpendicular to the path of radiation through said target area.

* * * * *

UNITED STATES PATENT AND TRADEMARK OFFICE
CERTIFICATE OF CORRECTION

PATENT NO. : 4,662,379

DATED : May 5, 1987

INVENTOR(S) : Albert Macovski

It is certified that error appears in the above-identified patent and that said Letters Patent is hereby corrected as shown below:

Amend Claim 1 to read as follows:

1. A method of imaging a blood vessel such as a coronary artery comprising the steps of
   providing radiation source means and radiation detector means on opposite sides of a target area and at a plurality of angular positions through the target area,
   [gating said radiation source means at said plurality of positions after administering a contrast agent intravenously]
   administering a contrast agent intravenously,
   gating said radiation source means based on a selected time using an electrocardiagram to obtain a first plurality of detector signals indicative of a first plurality of views through said target area, and
   tomosynthesisly combining said first plurality of detector signals to provide a planar image through said target area, said planar image being generally perpendicular to the path of radiation through said target area.

Signed and Sealed this

Fifth Day of April, 1988

Attest:

Attesting Officer

DONALD J. QUIGG

Commissioner of Patents and Trademarks

UNITED STATES PATENT AND TRADEMARK OFFICE
CERTIFICATE OF CORRECTION

PATENT NO. : 4,662,379
DATED : May 5, 1987
INVENTOR(S) : ALBERT MACOVSKI

It is certified that error appears in the above-identified patent and that said Letters Patent is hereby corrected as shown below:

On page 1, after the title, insert the following paragraph:

--This invention was made with Government support under contract No. N01-HV-02922 awarded by the Public Health Services. The Government has certain rights in this invention.--

Signed and Sealed this

Thirteenth Day of December, 1994

Attest:

BRUCE LEHMAN

*Attesting Officer*     *Commissioner of Patents and Trademarks*